United States Patent
Fridman

(10) Patent No.: US 8,889,160 B2
(45) Date of Patent: Nov. 18, 2014

(54) OPHTHALMIC COMPOSITIONS WITH BIGUANIDE AND PEG-GLYCEROL ESTERS

(71) Applicant: Bausch & Lomb Incorporated, Rochester, NY (US)

(72) Inventor: Krista Fridman, Penfield, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 13/886,571

(22) Filed: May 3, 2013

(65) Prior Publication Data
US 2013/0261190 A1 Oct. 3, 2013

Related U.S. Application Data

(62) Division of application No. 13/072,998, filed on Mar. 28, 2011, now Pat. No. 8,501,200.

(60) Provisional application No. 61/327,960, filed on Apr. 26, 2010.

(51) Int. Cl.
| | | |
|---|---|---|
| A61K 9/00 | (2006.01) | |
| A61K 31/155 | (2006.01) | |
| A61K 31/22 | (2006.01) | |
| A61K 31/69 | (2006.01) | |
| C11D 3/48 | (2006.01) | |
| A01N 35/10 | (2006.01) | |
| C11D 3/00 | (2006.01) | |
| C11D 3/20 | (2006.01) | |
| C11D 1/74 | (2006.01) | |
| A61L 12/14 | (2006.01) | |

(52) U.S. Cl.
CPC *A01N 35/10* (2013.01); *C11D 3/48* (2013.01); *A61L 12/147* (2013.01); *A61L 12/142* (2013.01); *C11D 3/0078* (2013.01); *C11D 3/2093* (2013.01); *C11D 1/74* (2013.01)

USPC .......................................................... 424/400

(58) Field of Classification Search
USPC ................... 424/400; 514/635, 546, 64, 912
See application file for complete search history.

(56) References Cited

U.S. PATENT DOCUMENTS

| | | |
|---|---|---|
| 4,758,595 A | 7/1988 | Ogunbiyi et al. |
| 5,965,088 A | 10/1999 | Lever et al. |
| 6,369,112 B1 * | 4/2002 | Xia ............................. 514/635 |
| 6,995,123 B2 | 2/2006 | Ketelson et al. |
| 8,324,171 B1 * | 12/2012 | Burke et al. ................ 514/20.8 |
| 2007/0207104 A1 * | 9/2007 | Borish ......................... 424/70.1 |
| 2008/0214421 A1 * | 9/2008 | Zhao et al. ................... 510/112 |
| 2008/0311070 A1 * | 12/2008 | Burke et al. .............. 424/78.04 |
| 2009/0036404 A1 * | 2/2009 | MacLeod ...................... 514/54 |

FOREIGN PATENT DOCUMENTS

WO  2004/112848 A1  12/2004

OTHER PUBLICATIONS

International Search Report in corresponding International Application No. PCT/US2011/033237 dated Aug. 25, 2011 (4 pages).
Written Opinion of the International Searching Authority in corresponding International Application No. PCT/US2011/033237 Aug. 25, 2011 (4 pages).
WARD: Superficial Punctate Fluorescein Staining of the Ocular Surface Optom & Vis Sci, dated Jan. 2008, vol. 85 (No. 1), pp. 8-16.

* cited by examiner

*Primary Examiner* — Gigi Huang
(74) *Attorney, Agent, or Firm* — Toan P. Vo

(57) ABSTRACT

Ophthalmic compositions comprising 0.5 ppm to 5 ppm of alexidine, and 0.005 wt. % to 0.3 wt. % of glycereth-18-ethylhexanoate. The invention is also directed to the use of the ophthalmic compositions to clean and disinfect contact lenses, and in particular, soft, silicone, hydrogel contact lenses.

13 Claims, 5 Drawing Sheets

OPHTHALMIC COMPOSITIONS WITH BIGUANIDE AND PEG-GLYCEROL ESTERS

CROSS REFERENCE

This application is a divisional application of U.S. patent application Ser. No. 13/072,998 filed Mar. 28, 2011, which in turn claims the benefit of Provisional Patent Application No. 61/327,960 filed Apr. 26, 2010, which is incorporated by reference herein.

The present invention relates to ophthalmic compositions that include a biguanide antimicrobial agent, e.g., poly(hexamethylene biguanide) and PEG-glycerol esters. The invention is also directed to the use of the ophthalmic compositions to clean and disinfect contact lenses.

BACKGROUND OF THE INVENTION

During normal use, contact lenses become soiled or contaminated with a wide variety of compounds that can degrade lens performance. For example, a contact lens will become soiled with biological materials such as proteins or lipids that are present in the tear fluid and which adhere to the lens surface. Also, by handling of the contact lens, sebum (skin oil) or cosmetics or other materials can soil the contact lens. These biological and external contaminants can affect visual acuity and patient comfort during use and at the end of the day. Accordingly, it is important to remove any debris from the lens surface for continued comfortable use with a lens care solution that contains one or more cleaning components.

Ophthalmic compositions formulated as a lens care solution must also contain one or more disinfectant components. Presently, the two most popular disinfectant components are poly(hexamethylene biguanide), at times referred to as PHMB or PAPB, and polyquaternium-1.

As stated, PHMB is presently used in contact, lens care solutions. These PHMB-based care solutions represent a significant improvement in patient comfort and antimicrobial effectiveness compared to most other antimicrobial components. However, as with any antimicrobial component there remains a tradeoff between the concentration of the antimicrobial component in the solution and the comfort experienced by the patient. Due to its wide commercial acceptance, extensive efforts have been directed to improve the antimicrobial efficacy or the comfort level to the patient by chemically modifying PHMB or by using a secondary component to enhance or supplement the efficacy profile of a lens care solution.

Beginning in the 1980's, with the growing market of contact lens use, the number of descriptive case studies of superficial punctate corneal staining has increased in the scientific literature. Clinicians are cautioned, however, not to extrapolate from the clear clinical significance of high intensity, gross staining associated with corneal lesions and disease down to the meaning of superficial punctate corneal staining. Superficial punctate patterns of fluorescein dye fluorescence are to be viewed differently from nonsuperficial coalesced injury-related staining based on their common characteristics (superficial, transient and asymptomatic). For an extensive background and review on this subject, one is referred to Ward, K. W., "*Superficial Punctate Fluorescein Staining of the Ocular Surface*", Optometry and Vision Science 2008, 85(1) 1. Although the precise mechanisms that control the depth and extent of the fluorescence signal associated with superficial punctate corneal staining remains unclear, the studies as a whole do provide scientific support that such staining does not reflect corneal injury or toxicity. In fact, both epidemiological and experimental evidence demonstrates a lack of correlation between superficial punctate corneal staining and the institution of corneal infections. Nevertheless, there have been a few reports that attempt to characterize the intensity of superficial punctate corneal staining at 2-hours with corneal toxicity, or imply that there exists a correlation between such staining and the institution of corneal infections. Again, these reports offer no scientific or clinical data to support such assertions.

To alleviate any such concerns that may exist in the lens care solution market, Applicants sought out and developed ophthalmic compositions that exhibit relatively low, superficial punctate corneal staining following placement of hydrogel contact lenses soaked with the compositions. The solutions must also provide an accepted level of patient comfort, particularly upon insertion of a contact lens. In fact, head-to-head the ophthalmic compositions described herein meet or exceed the superficial punctate corneal staining profile and comfort profile of the leading lens care solutions presently on the market. More importantly, lens care solutions that are to be placed in the market place should exceed the present FDA/ISO standards, some unfortunately do not.

SUMMARY OF THE INVENTION

The invention is directed to ophthalmic compositions comprising 0.5 ppm to 5 ppm of alexidine, and 0.005 wt. % to 0.3 wt. % of glycereth-18-ethylhexanoate. The invention is also directed to the use of the ophthalmic compositions to clean and disinfect contact lenses, and in particular, soft, silicone, hydrogel contact lenses.

BRIEF DESCRIPTION OF THE DRAWINGS

The invention will be better understood from the following description and in consideration with the accompanying figures. It is to be expressly understood, however, that each of the figures is provided to further illustrate and describe the invention and is not intended to further limit the invention claimed.

DETAILED DESCRIPTION OF THE INVENTION

Figure 1:
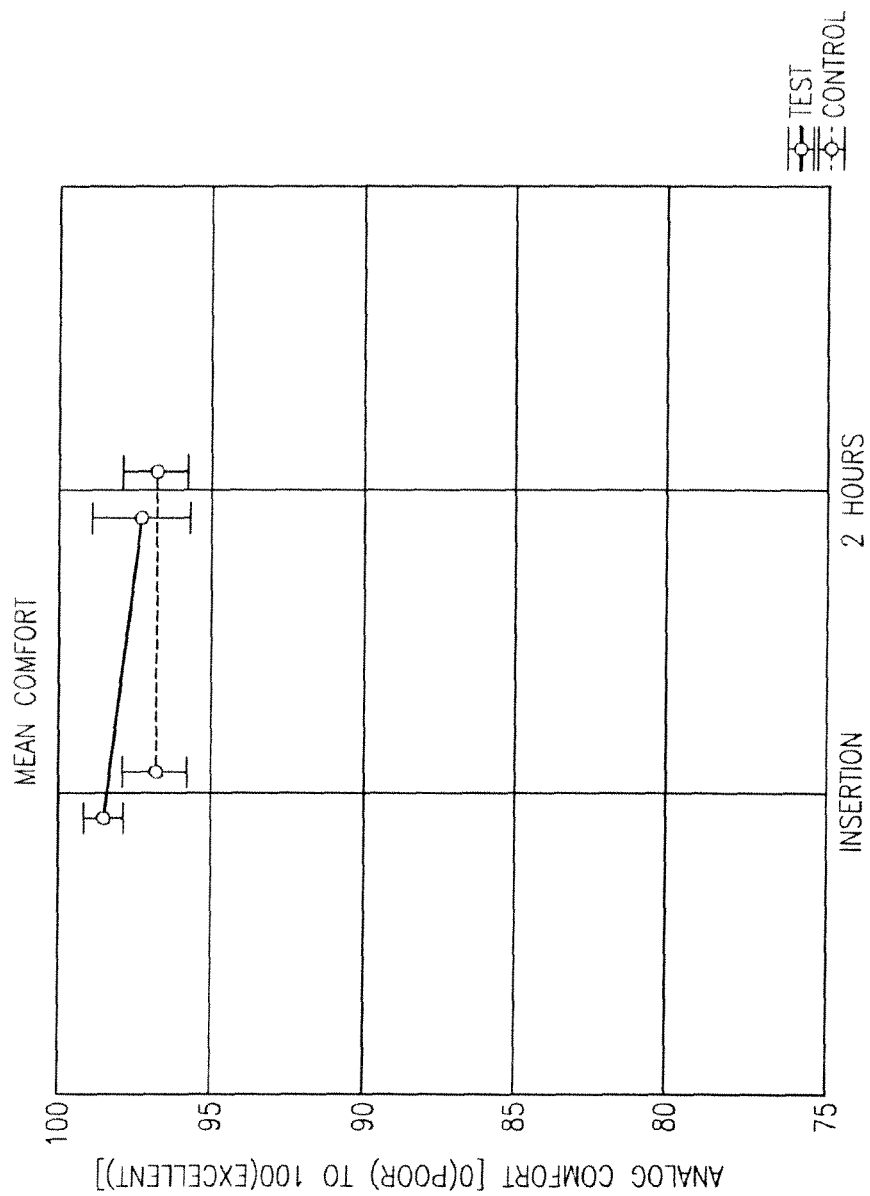
FIG. 1 is a plot showing a clinical comparison between a test solution and control solution for comfort at insertion of a contact lens and after two hours.

Applicants and others at Bausch & Lomb have developed and tested numerous ophthalmic formulations for use as lens care solutions. As mentioned above, such lens care solutions must satisfy a number of functional characteristics. First, the solutions must possess the cleaning ability to remove denatured tear proteins and tear lipids as well as other external contaminants. Second, the solutions must possess significant disinfecting ability against a number of different bacteria and fungal strains. Third, the solutions must remain comfortable to the contact lens patient with minimal stinging as well as provide a platform to provide additional comfort or protection to the ocular surface. Lastly, the solutions must not cause significant shrinkage or swelling of the many different contact lens materials, which in turn can lead to loss in visual acuity and unwanted or pronounced lens movement.

U.S. Patent Publication No. 2007/0207104 describes a family of PEG-glycerol esters and the inclusion of such compounds in a variety of personal care products including soaps or shampoos, and lotions such as sunscreen or moisturizing products. The compounds are said to possess antimicrobial properties though Applicants observed no evidence of such activity against the bacteria and fungi of interest for ophthalmic applications and at the concentrations tested, i.e., up to 0.6% by weight. As indicated in Table 1 below several borate-buffered saline (BBS) solutions were prepared with varying concentrations of glycereth-18-ethylhexanoate, referred to in the literature as HestG-18-O™. The BBS solutions containing the glycereth-18-ethylhexanoate showed no difference in antimicrobial activity relative to BBS alone against the listed bacteria and fungi.

In spite of the disappointing antimicrobial data of Table 1, Applicants continued to formulate aqueous ophthalmic solutions that contained glycereth-18-ethylhexanoate. Applicants tested ophthalmic solutions that contained glycereth-18-ethylhexanoate and one or more antimicrobial components. BBS solutions were prepared containing 0.3 wt. % glycereth-18-ethylhexanoate and PHMB and/or polyquaternium-1. Surprisingly, only the BBS solution containing PHMB (1.3 ppm) and the glycereth-18-ethylhexanoate (0.3 wt. %) showed an enhancement in antimicrobial activity against the tested organisms, Table 2. In contrast, there was no enhancement in antimicrobial activity in BSS solutions that contained glycereth-18-ethylhexanoate (0.3 wt. %) and polyquaternium-1 (5 ppm). Solution Nos. 8 to 12 are embodiments of the invention whereas Solution Nos. 1 to 7 are comparative solutions.

TABLE 1

BBS solutions with glycereth-18-ethylhexanoate.

| Solution No. HestG-18-O (wt. %) | S. aureus | P. aeruginosa | S. marcescens | C. albicans | F. solani |
|---|---|---|---|---|---|
| BBS | 1.4 | 1.2 | 1.2 | 0.6 | 0.8 |
| 1 (0.6) | 1.4 | 1.2 | 1.2 | 0.7 | 0.8 |
| 2 (0.3) | 1.4 | 1.2 | 1.2 | 0.5 | 0.7 |
| 3 (0.3) | 1.4 | 1.2 | 1.2 | 0.7 | 0.8 |
| 4 (0.1) | 1.4 | 1.2 | 1.3 | 0.5 | 0.7 |

TABLE 2

BBS solutions with glycereth-18-ethylhexanoate and PHMB/PQ-1.

| Solution No. Hest G-18-O (wt. %) | S. aureus | P. aeruginosa | S. marcescens | C. albicans | F. solani |
|---|---|---|---|---|---|
| BBS | 1.4 | 1.2 | 1.2 | 0.6 | 0.8 |
| 5 BBS + PQ-1 | 4.3 | >4.7 | 3.4 | 0.8 | 2.8 |
| 6 PQ-1/(0.3) | 4.9 | >4.7 | 3.5 | 0.6 | 2.8 |
| 7 BBS + PHMB | 2.7 | 3.5 | 2.4 | 2.4 | 2.0 |

TABLE 2-continued

BBS solutions with glycereth-18-ethylhexanoate and PHMB/PQ-1.

| Solution No. Hest G-18-O (wt. %) | S. aureus | P. aeruginosa | S. marcescens | C. albicans | F. solani |
|---|---|---|---|---|---|
| 8 PHMB/(0.3) | 4.2 | >4.7 | 4.7 | 3.5 | 3.5 |
| 9 PHMB/(0.01) | 3.7 | 4.0 | 3.3 | 3.4 | 3.3 |
| 10 PHMB/(0.05) | >4.8 | 4.5 | 4.0 | 3.8 | 3.9 |
| 11 PHMB/(0.1) | >4.8 | >4.7 | 4.4 | 2.6 | 4.1 |
| 12 PHMB/(0.15) | >4.8 | >4.7 | 4.6 | 4.2 | 4.1 |

The invention is directed to an ophthalmic composition comprising: 0.1 ppm to 2 ppm of poly(hexamethylene biguanide); and 0.005 wt. % to 0.3 wt. % of a PEG-glycerol ester of general formula I

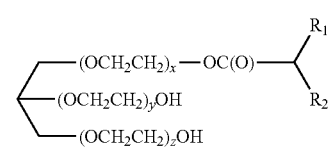

wherein $R_1$ is a $C_3$-$C_8$ alkyl and $R_2$ is H or a $C_1$-$C_4$ alkyl; and x+y+z has an average value from 8 to 30. In a particular embodiment, $R_1$ is a $C_4$-$C_6$ alkyl and $R_2$ is ethyl. Also, in many embodiments, the average value of x+y+z is from 14 to 22.

To provide additional lubricating and moisturizing characteristics to the ophthalmic compositions, the compositions can also include what are referred to in the art as comfort agents. Suitable comfort components include, but are not limited to, water soluble natural gums, cellulose-derived polymers and the like. Useful natural gums include guar gum, gum tragacanth and the like. Useful cellulose-derived comfort components include cellulose-derived polymers, such as hydroxypropyl cellulose, hydroxypropylmethyl cellulose, carboxymethyl cellulose, methyl cellulose, hydroxyethyl cellulose and the like. A very useful comfort component is hydroxypropylmethyl cellulose (HPMC). Some non-cellulose comfort components include propylene glycol or glycerin. The comfort components are typically present in the solution from 0.01% to 1% (w/v).

Hyaluronic acid is a linear polysaccharide (long-chain biological polymer) formed by repeating disaccharide units consisting of D-glucuronic acid and N-acetyl-D-glucosamine linked by β(1-3) and β(1-4) glycosidic linkages. Hyaluronic acid is distinguished from the other glycosaminoglycans, as it is free from covalent links to protein and sulphonic groups. Hyaluronic acid is ubiquitous in animals, with the highest concentration found in soft connective tissue. It plays an important role for both mechanical and transport purposes in the body; e.g., it gives elasticity to the joints and rigidity to the vertebrate disks, and it is also an important component of the vitreous body of the eye.

Hyaluronic acid is accepted by the ophthalmic community as a compound that can protect biological tissues or cells from compressive forces. Accordingly, hyaluronic acid has been proposed as one component of a viscoelastic ophthalmic composition for cataract surgery. The viscoelastic properties of hyaluronic acid, that is, hard elastic under static conditions though less viscous under small shear forces enables hyaluronic acid to basically function as a shock absorber for cells and tissues. Hyaluronic acid also has a relatively large capacity to absorb and hold water. The stated properties of hyaluronic acid are dependent on the molecular weight, the solution concentration, and physiological pH. At low concentrations, the individual chains entangle and form a continuous network in solution, which gives the system interesting properties, such as pronounced viscoelasticity and pseudoplasticity that is unique for a water-soluble polymer at low concentration.

One other preferred comfort agent that is believed to maintain a hydrated corneal surface is polyvinylpyrrolidone (PVP). PVP is a linear homopolymer or essentially a linear homopolymer comprising at least 90% repeat units derived from 1-vinyl-2-pyrrolidone monomer the remainder of the monomer composition can include neutral monomer, e.g., vinyl or acrylates. Other synonyms for PVP include povidone, polyvidone, 1-vinyl-2-pyrolidinone, and 1-ethenyl-2-pyrolionone (CAS registry number 9003-39-8). The PVP will preferably have a weight average molecular weight from 10,000 to 250,000 or from 30,000 to 100,000. Such materials are sold by various companies, including ISP Technologies, Inc. under the trademark PLASDONE®K-29/32, from BASF under the trademark KOLLIDON®, for example, KOLLIDON® K-30 or K-90. It is also preferred that one use pharmaceutical grade PVP.

As stated, the compositions will also include a polymeric biguanide known as poly(hexamethylene biguanide) (PHMB or PAPB). A commercial source of PHMB can be obtained from Arch Chemicals, Inc., Norwalk, Conn. under the trademark Cosmocil™ CQ. The PHMB is present in the compositions from 0.2 ppm to 2 ppm or from 0.5 ppm to 1.3 ppm. Another biguanide of interest is 1,1'-hexamethylene-bis[5-(2-ethylhexyl)biguanide], which is referred to in the art as "alexidine". The alexidine is present in the compositions from 0.5 ppm to 5 ppm or from 0.5 ppm to 2 ppm.

In one embodiment, the hyaluronic acid is present from 0.002 wt. % to 0.04 wt. %, and the cationic, antimicrobial component is poly(hexamethylene biguanide). Accordingly, one of the more preferred compositions comprises 0.5 ppm to 1.3 ppm of poly(hexamethylene biguanide), 0.01 wt. % to 0.1 wt. % of a PEG-glycerol esters of general formula I, and 0.002 wt. % to 0.04 wt. % hyaluronic acid.

The compositions can also include one of the more common quaternary ammonium compounds, e.g., α-[4-tris(2-hydroxyethyl)-ammonium chloride-2-butenyl]poly[1-dimethyl ammonium chloride-2-butenyl]-ω-tris(2-hydroxyethyl) ammonium chloride, also referred to in the art as polyquaternium-1. Quaternary ammonium compounds are generally referred to in the art as "polyquaternium" disinfectants, and are identified by a particular number following the designation such as polyquaternium-1, polyquaternium-10 or polyquaternium-42. Polyquaternium-1 is present in the ophthalmic compositions from 0.5 ppm to 3 ppm. Polyquaternium-42 is also one of the more preferred polyquaternium disinfectants, see, U.S. Pat. No. 5,300,296. Polyquaternium-42 is present in the ophthalmic compositions from 5 ppm to 50 ppm.

It is to be understood by those in the art that the compositions can include one or more of the antimicrobial components described above. For example, in one embodiment, the ophthalmic compositions include polyquaternium-1 in combination with a biguanide antimicrobial component such as poly(hexamethylene biguanide). The polyquaternium-1 is present in relatively low concentrations, that is, from 0.5 ppm to 3 ppm, relative to the reported concentration of polyquaternium-1 in both Opti-Free® Express and Opti-Free®Replenish. Applicants believe that the polyquaternium-1 and the PHMB, in combination, may enhance the biocidal profile of the ophthalmic compositions.

Contact Lens Care Compositions

The contact lens care solutions will very likely include a buffer system. By the terms "buffer" or "buffer system" is meant a compound that, usually in combination with at least one other compound, provides a buffering system in solution that exhibits buffering capacity, that is, the capacity to neutralize, within limits, either acids or bases (alkali) with relatively little or no change in the original pH. Generally, the buffering components are present from 0.05% to 2.5% (w/v) or from 0.1% to 1.5% (w/v).

The term "buffering capacity" is defined to mean the millimoles (mM) of strong acid or base (or respectively, hydrogen or hydroxide ions) required to change the pH by one unit when added to one liter (a standard unit) of the buffer solution. The buffer capacity will depend on the type and concentration of the buffer components. The buffer capacity is measured from a starting pH of 6 to 8, preferably from 7.4 to 8.4.

Borate buffers include, for example, boric acid and its salts, for example, sodium borate or potassium borate. Borate buffers also include compounds such as potassium tetraborate or potassium metaborate that produce borate acid or its salt in solutions. Borate buffers are known for enhancing the efficacy of certain polymeric biguanides. For example, U.S. Pat. No. 4,758,595 to Ogunbiyi et al. describes that a contact-lens solution containing PHMB can exhibit enhanced efficacy if combined with a borate buffer.

A phosphate buffer system preferably includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The phosphate buffer components frequently are used in amounts from 0.01% or to 0.5% (w/v), calculated as phosphate ion.

Other known buffer compounds can optionally be added to the lens care compositions, for example, citrates, citric acid, sodium bicarbonate, TRIS, and the like. Other ingredients in the solution, while having other functions, may also affect the buffer capacity, e.g., propylene glycol or glycerin.

A preferred buffer system is based upon boric acid/borate, a mono and/or dibasic phosphate salt/phosphoric acid or a combined boric/phosphate buffer system. For example a combined boric/phosphate buffer system can be formulated from a mixture of boric acid/sodium borate and a monobasic/dibasic phosphate. In a combined boric/phosphate buffer system, the phosphate buffer is used (in total) at a concentration of 0.004 to 0.2 M (Molar), preferably 0.04 to 0.1 M. The borate buffer (in total) is used at a concentration of 0.02 to 0.8 M, preferably 0.07 to 0.2 M.

The lens care solutions can also include an effective amount of a surfactant component, a viscosity inducing or thickening component, a chelating or sequestering component, or a tonicity component. The additional component or components can be selected from materials which are known to be useful in contact lens care solutions and are included in amounts effective to provide the desired functional characteristic.

Suitable surfactants can be cationic or nonionic, and are typically present (individually or in combination) in amounts up to 2% w/v. One preferred surfactant class are the nonionic surfactants. The surfactant should be soluble in the lens care solution and non-irritating to eye tissues. Many nonionic surfactants comprise one or more chains or polymeric components having oxyalkylene (—O—R—) repeats units wherein R has 2 to 6 carbon atoms. Preferred non-ionic surfactants comprise block polymers of two or more different kinds of oxyalkylene repeat units, which ratio of different repeat units determines the HLB of the surfactant. Satisfactory non-ionic surfactants include polyethylene glycol esters of fatty acids, e.g. coconut, polysorbate, polyoxyethylene or polyoxypropylene ethers of higher alkanes ($C_{12}$-$C_{18}$). Examples of this class include polysorbate 20 (available under the trademark Tween® 20), polyoxyethylene (23) lauryl ether (Brij® 35), polyoxyethyene (40) stearate (Myrj®52), polyoxyethylene (25) propylene glycol stearate (Atlas® G 2612). Still another preferred surfactant is tyloxapol.

A particular non-ionic surfactant consisting of a poly(oxypropylene)-polyoxyethylene) adduct of ethylene diamine having a molecular weight from about 6,000 to about 24,000 daltons wherein at least 40 weight percent of said adduct is poly(oxyethylene) has been found to be particularly advantageous for use in cleaning and conditioning both soft and hard contact lenses. The CTFA Cosmetic Ingredient Dictionary's adopted name for this group of surfactants is poloxamine. Such surfactants are available from BASF Wyandotte Corp., Wyandotte, Mich., under Tetronic®. Particularly good results are obtained with poloxamine 1107 or poloxamine 1304. The foregoing poly(oxyethylene) poly(oxypropylene) block polymer surfactants will generally be present in a total amount from 0.0 to 2% w/v, from 0. to 1% w/v, or from 0.2 to 0.8% w/v An analogous of series of surfactants, for use in the lens care compositions, is the poloxamer series which is a poly (oxyethylene) poly(oxypropylene) block polymers available under Pluronic® (commercially available form BASF). In accordance with one embodiment of a lens care composition the poly(oxyethylene)-poly(oxypropylene) block copolymers will have molecular weights from 2500 to 13,000 daltons or from 6000 to about 12,000 daltons. Specific examples of surfactants which are satisfactory include: poloxamer 108, poloxamer 188, poloxamer 237, poloxamer 238, poloxamer 288 and poloxamer 407. Particularly good results are obtained with poloxamer 237 or poloxamer 407. The foregoing poly(oxyethylene) poly(oxypropylene) block polymer surfactants will generally be present in a total amount from 0.0 to 2% w/v, from 0. to 1% w/v, or from 0.2 to 0.8% w/v.

In another embodiment, the surfactant is a an amphoteric surfactant of general formula II

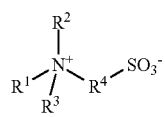

II wherein $R^1$ is R or —$(CH_2)_n$—NHC(O)R, wherein R is a $C_8$-$C_{16}$alkyl optionally substituted with hydroxyl and n is 2, 3 or 4; $R^2$ and $R^3$ are each independently selected from methyl, ethyl, propyl or iso-propyl; and $R^4$ is a $C_2$-$C_8$alkylene optionally substituted with hydroxyl. Alternatively, one can use a hydroxysulfobetaine of general formula III

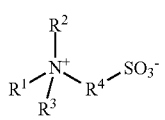

III wherein R is a $C_8$-$C_{16}$alkyl substituted with at least one hydroxyl; $R^2$ and $R^3$ are each independently selected from methyl, ethyl, propyl or iso-propyl; and $R^4$ is a $C_2$-$C_8$alkylene substituted with at least one hydroxyl.

The lens care solutions can also include a phosphonic acid, or its physiologically compatible salt, that is represented by the following formula:

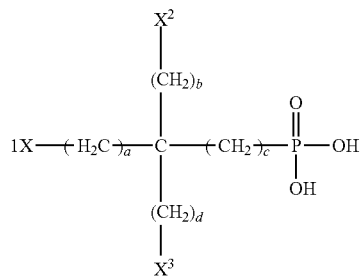

wherein each of a, b, c, and d are independently selected from integers from 0 to 4, preferably 0 or 1; $X^1$ is a phosphonic acid group (i.e., P(OH)$_2$O), hydroxy, amine or hydrogen; and $X^2$ and $X^3$ are independently selected from the group consisting of halogen, hydroxy, amine, carboxy, alkylcarbonyl, alkoxycarbonyl, or substituted or unsubstituted phenyl, and methyl. Exemplary substituents on the phenyl are halogen, hydroxy, amine, carboxy and/or alkyl groups. A particularly preferred species is that wherein a, b, c, and d in are zero, specifically the tetrasodium salt of 1-hydroxyethylidene-1,1-diphosphonic acid, also referred to as tetrasodium etidronate, commercially available from Monsanto Company as DeQuest® 2016 diphosphonic acid sodium salt or phosphonate.

The lens care solutions can include dexpanthenol, which is an alcohol of pantothenic acid, also called Provitamin B5, D-pantothenyl alcohol or D-panthenol. It has been stated that dexpanthenol may play a role in stabilizing the lachrymal film at the eye surface following placement of a contact lens on the eye. Dexpanthenol is preferably present in the solution in an amount from 0.2 to 5%/v, from 0.5 to 3% w/v, or from 1 to 2% w/v.

The contact lens care solutions can also include a sugar alcohol such as sorbitol or xylitol. Typically, dexpanthenol is used in combination with the sugar alcohol. The sugar alcohol is present in the lens care compositions in an amount from 0.4 to 5% w/v or from 0.8 to 3% w/v.

The lens care solutions can also include one or more chelating components to assist in the removal of lipid and protein deposits from the lens surface following daily use. Typically, the ophthalmic compositions will include relatively low amounts, e.g., from 0.005% to 0.05% (w/v) of ethylenediaminetetraacetic acid (EDTA) or the corresponding metal salts thereof such as the disodium salt, $Na_2EDTA$.

One possible alternative to the chelator $Na_2EDTA$ or a possible combination with $Na_2EDTA$, is a disuccinate of formula IV below or a corresponding salt thereof;

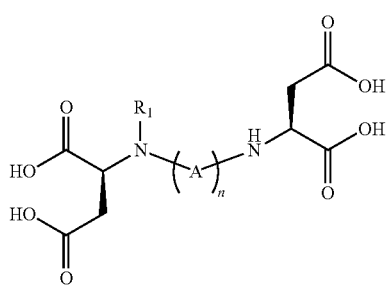

IV wherein $R_1$ is selected from hydrogen, alkyl or —C(O)alkyl, the alkyl having one to twelve carbons and optionally one or more oxygen atoms, A is a methylene group or an oxyalkylene group, and n is from 2 to 8. In one embodiment, the disuccinate is S,S-ethylenediamine disuccinate (S,S-EDDS) or a corresponding salt thereof. One commercial source of S,S-EDDS is represented by Octaquest® E30, which is commercially available from Octel. The chemical structure of the trisodium salt of S,S-EDDS is shown below. The salts can also include the alkaline earth metals such as calcium or magnesium. The zinc or silver salt of the disuccinate can also be used in the ophthalmic compositions.

Still another class of chelators include alkyl ethylenediaminetriacetates such as nonayl ethylenediaminetriacetate. See, U.S. Pat. No. 6,995,123 for a more complete description of such agents.

The lens care solutions will typically include an effective amount of a tonicity adjusting component. Among the suitable tonicity adjusting components that can be used are those conventionally used in contact lens care products such as various inorganic salts. Sodium chloride and/or potassium chloride and the like are very useful tonicity components. The amount of tonicity adjusting component is effective to provide the desired degree of tonicity to the solution.

The lens care solutions will typically have an osmolality in the range of at least about 200 mOsmol/kg for example, about 300 or about 350 to about 400 mOsmol/kg. The lens care solutions are substantially isotonic or hypertonic (for example, slightly hypertonic) and are ophthalmically acceptable.

One exemplary ophthalmic composition is formulated as a contact lens disinfecting solution prepared with the components and amounts of each listed in Tables 3 and 4.

TABLE 3

| Component | Minimum Amount (wt. %) | Maximum Amount (wt. %) | Preferred Amount (wt. %) |
|---|---|---|---|
| boric acid | 0.10 | 1.0 | 0.64 |
| sodium borate | 0.01 | 0.20 | 0.1 |
| sodium chloride | 0.05 | 1.0 | 0.5 |
| PEG-glycerol ester | 0.005 | 0.50 | 0.04 |
| hyaluronic acid | 0.005 | 0.05 | 0.01 |
| Tetronic ® 1107 | 0.05 | 1.2 | 0.6 |
| S,S-EDDS | 0.005 | 0.15 | 0.05 |
| PHMB | 0.4 ppm | 2 ppm | 1.3 ppm |
| polyquaternium-1 | 0.5 ppm | 5 ppm | 1 ppm |

TABLE 4

| Component | Minimum Amount (wt. %) | Maximum Amount (wt. %) | Preferred Amount (wt. %) |
|---|---|---|---|
| boric acid | 0.10 | 1.0 | 0.64 |
| sodium borate | 0.01 | 0.20 | 0.09 |
| sodium chloride | 0.05 | 1.0 | 0.5 |
| HEST G-18-O | 0.005 | 0.50 | 0.05 |
| Tetronic ® 1107 | 0.05 | 1.0 | 0.5 |
| Dequest ® 2016 | 0.01 | 0.5 | 0.1 |
| Na$_2$EDTA | 0.005 | 0.15 | 0.05 |
| PHMB | 0.4 ppm | 2 ppm | 1.1 ppm |

Another contact lens solution includes the following ingredients listed in Table 5.

TABLE 5

| Component | Minimum Amount (wt. %) | Maximum Amount (wt. %) | Preferred Amount (wt. %) |
|---|---|---|---|
| sorbitol or xylitol | 0.5 | 5 | 3 |
| poloxamer 407 | 0.05 | 1.0 | 0.10 |
| sodium phosphate, dihydrogen | 0.10 | 0.8 | 0.46 |
| PEG-glycerol ester | 0.005 | 0.5 | 0.10 |
| hyaluronic acid | 0.005 | 0.03 | 0.01 |
| Na$_2$EDTA | 0.005 | 0.15 | 0.05 |
| PHMB | 0.2 ppm | 2 ppm | 1 ppm |

Other contact lens solutions according includes the following ingredients listed in Tables 6 and 7.

TABLE 6

| Component | Minimum Amount (wt. %) | Maximum Amount (wt. %) | Preferred Amount (wt. %) |
|---|---|---|---|
| PEG-glycerol ester | 0.005 | 0.50 | 0.10 |
| propylene glycol | 0.1 | 1.0 | 0.50 |
| poloxamer 237 | 0.01 | 0.20 | 0.05 |
| phosphate monobasic | 0.05 | 0.40 | 0.10 |
| phosphate dibasic | 0.05 | 0.4 | 0.12 |
| hyaluronic acid | 0.005 | 0.02 | 0.008 |
| S,S-EDDS | 0.005 | 0.2 | 0.06 |
| PHMB | 0.2 ppm | 2 ppm | 1.1 ppm |
| polyquaternium-1 | 0.5 ppm | 3 ppm | 1 ppm |

TABLE 7

| Component | Minimum Amount (wt. %) | Maximum Amount (wt. %) | Preferred Amount (wt. %) |
|---|---|---|---|
| PEG-glycerol ester | 0.005 | 0.50 | 0.10 |
| Tetronics ® 1304 | 0.01 | 0.2 | 0.05 |
| boric acid | 0.1 | 1.0 | 0.60 |
| sodium citrate | 0.01 | 0.4 | 0.15 |
| hydroxypropyl guar | 0.01 | 0.5 | 0.05 |
| Na$_2$EDTA | 0.02 | 0.1 | 0.05 |
| polyquaternium-1 | 0.5 ppm | 10 ppm | 5 ppm |

As described, the ophthalmic compositions can be used to clean and disinfect contact lenses. In general, the contact lens solutions can be used as a daily or every other day care regimen known in the art as a "no-rub" regimen. This procedure includes removing the contact lens from the eye, rinsing both sides of the lens with a few milliliters of solution and placing the lens in a lens storage case. The lens is then immersed in fresh solution for at least two hours. The lens is the removed form the case, optionally rinsed with more solution, and repositioned on the eye.

Alternatively, a rub protocol would include each of the above steps plus the step of adding a few drops of the solution to each side of the lens, followed by gently rubbing the surface between ones fingers for approximately 3 to 10 seconds. The lens can then be, optionally rinsed, and subsequently immersed in the solution for at least two hours. The lenses are removed from the lens storage case and repositioned on the eye.

The ophthalmic compositions can be used with many different types of contact lenses including: (1) hard lenses formed from materials prepared by polymerization of acrylic esters, such as poly(methyl methacrylate) (PMMA), (2) rigid gas permeable (RGP) lenses formed from silicone acrylates and fluorosilicone methacrylates, (3) soft, hydrogel lenses, and (4) non-hydrogel elastomer lenses.

As an example, soft hydrogel contact lenses are made of a hydrogel polymeric material, a hydrogel being defined as a crosslinked polymeric system containing water in an equilibrium state. In general, hydrogels exhibit excellent biocompatibility properties, i.e., the property of being biologically or biochemically compatible by not producing a toxic, injurious or immunological response in a living tissue. Representative conventional hydrogel contact lens materials are made by polymerizing a monomer mixture comprising at least one hydrophilic monomer, such as (meth)acrylic acid, 2-hydroxyethyl methacrylate (HEMA), glyceryl methacrylate, N,N-dimethacrylamide, and N-vinylpyrrolidone (NVP). In the case of silicone hydrogels, the monomer mixture from which the copolymer is prepared further includes a silicone-containing monomer, in addition to the hydrophilic monomer. Generally, the monomer mixture will also include a crosslink monomer such as ethylene glycol dimethacrylate, tetraethylene glycol dimethacrylate, and methacryloxyethyl vinylcarbonate. Alternatively, either the silicone-containing monomer or the hydrophilic monomer may function as a crosslink agent.

The ophthalmic compositions can also be formulated as a contact lens rewetting eye drop solution. By way of example, the rewetting drops may be formulated according to any one of the foregoing formulations of Tables 1 to 5 above. Alternatively, the formulations may be modified by increasing the amount of surfactant; by reducing the amount of antimicrobial agent to a preservative amount and/or by adding a humectant and/or demulcent.

The ophthalmic compositions can be used as a preservative in formulations for treating patients with dry eye. In such a method, the ophthalmic composition is administered to the patient's eye, eye lid or to the skin surrounding the patient's eye. The compositions can be administered to the eyes irrespective of whether contact lenses are present in the eyes of the patient. For example, many people suffer from temporary or chronic eye conditions in which the eye's tear system fails to provide adequate tear volume or tear film stability necessary to remove irritating environmental contaminants such as dust, pollen, or the like.

The ophthalmic compositions can also be used as a preservative in pharmaceutical compositions such as nasal sprays, ear and eye drops, suppositories, and prescription and over-the-counter formulations containing a pharmaceutical active that are used or administered over time such as a cream, ointment, gel or solution.

In many instances, the ophthalmic compositions will include one or more active pharmaceutical agents. Generally, the active pharmaceutical agent is in one or more classes of ocular pharmaceuticals including, but not limited to anti-inflammatory agents, antibiotics, immunosuppressive agents, antiviral agents, antifungal agents, anesthetics and pain killers, anticancer agents, anti-glaucoma agents, peptide and proteins, anti-allergy agents.

Example Nos. 1 to 4

Contact lens compositions of Example Nos. 1 to 4 of Table 8 are prepared using the following process (components are listed in wt. % unless noted in ppm). A volume of purified water equivalent to 70-90% of the total batch weight is added to a stainless steel mixing vessel. The following batch quantities of components are added to the water with stirring in the order listed: sodium chloride, edetate disodium, boric acid, sodium borate, Dequest® 2016 (if required) and Tetronics® 1107. The solution is mixed (stirred) for not less than 10 minutes to ensure complete dissolution of each of the components. If sodium hyaluronate is to be added, the solution is warmed to a temperature not less than 70° C. and then the sodium hyaluronate is added. The warmed solution is stirred for at least 20 minutes until the sodium hyaluronate appears to be completely dissolved. The pH of the resulting solution is measured at room temperature, and if necessary, the pH is adjusted with 1N NaOH or 1N HCl (target pH=7.5). In a second stainless steel vessel, a measured amount a measured amount of PAPB required for the batch is added to a given amount of purified water, and the solution is stirred for at least 10 minutes. In a third stainless steel vessel, a measured amount of polyquaternium-1, if required, is added to a given amount of purified water, and the solution is stirred for at least 10 minutes. The final solution is stirred for at least 15 minutes.

Biocidal Stand-Alone Stability

In order to assess the activity of the formulation, samples of Example No. 5 were bottled in 4 oz PET containers and stored at ambient temperature, as well as elevated temperatures for a given period. The stand-alone biocidal efficacy of the samples is tested at designated intervals to determine the stability of the formulation with time for disinfection activity, see Table 7. The "Stand-Alone Procedure for Disinfecting Products" is based on the Disinfection Efficacy Testing for Products dated May 1, 1997, prepared by the U.S. Food and Drug Administration, Division of Ophthalmic Devices. This performance requirement does not contain a rub procedure.

The stand-alone test challenges a disinfecting product with a standard inoculum of a representative range of microorganisms and establishes the extent of viability loss at predetermined time intervals comparable with those during which the product may be used. The primary criteria for a given disinfection period (corresponding to a potential minimum recommended disinfection period) is that the number of bacteria recovered per mL must be reduced by a mean value of not less than 3.0 logs within the given disinfection period. The number of mold and yeast recovered per ml must be reduced by a mean value of not less than 1.0 log within the minimum recommended disinfection time with no increase at four times the minimum recommended disinfection time.

The antimicrobial efficacy of each of the various compositions for the chemical disinfection and cleaning of contact lenses are evaluated in the presence of 10% organic soil using the stand-alone procedure. Microbial challenge inoculums are prepared using *Staphylococcus aureus* (ATCC 6538), *Pseudomonas aeruginosa* (ATCC 9027), *Serratia marcescens* (ATCC 13880), *Candida albicans* (ATCC 10231) and *Fusarium solani* (ATCC 36031). The test organisms are cultured on appropriate agar and the cultures are harvested using sterile Dulbecco's Phosphate Buffered Saline plus 0.05 percent weight/volume polysorbate 80 (DPBST) or a suitable diluent and transferred to a suitable vessel. Spore suspensions are filtered through sterile glass wool to remove hyphal fragments. *Serratia marcescens*, as appropriate, is filtered through a 1.2 µm filter to clarify the suspension.

TABLE 8

| Example | 1 | 2 | 3 | 4 | 5 |
|---|---|---|---|---|---|
| boric acid | 0.60 | 0.55 | 0.64 | 0.64 | 0.64 |
| sodium borate | 0.105 | 0.11 | 0.12 | 0.09 | 0.9 |
| sodium chloride | 0.50 | 0.45 | 0.50 | 0.50 | 0.5 |
| Na$_2$EDTA | 0.11 | 0.11 | 0.06 | 0.05 | 0.05 |
| Dequest ®2016 | 0.05 | 0.1 | — | 0.1 | 0.1 |
| Tetronics ®1107 | 0.5 | 0.5 | 0.6 | 0.5 | 0.5 |
| sodium hyaluronate | 0.01 | 0.008 | 0.01 | — | — |
| HEST ™ G-18-O | 0.05 | 0.05 | 0.05 | 0.05 | 0.05 |
| PAPB (ppm) | 1.3 | 0.8 | 1.1 | 1.1 | 1.3 |
| polyquaternium-1 (ppm) | — | 1.0 | 1.0 | — | — |

After harvesting, the suspension is centrifuged at no more than 5000×g for a maximum of 30 minutes at a temperature of 20° C. to 25° C. The supernatant is decanted and resuspended in DPBST or other suitable diluent. The suspension is centrifuged a second time, and resuspended in DPBST or other suitable diluent. All challenge bacterial and fungal cell suspensions are adjusted with DPBST or other suitable diluent to $1\times10^7$ to $1\times10^8$ cfu/mL. The appropriate cell concentration may be estimated by measuring the turbidity of the suspension, for example, using a spectrophotometer at a preselected wavelength, for example, 490 nm. One tube is prepared containing a minimum of 10 mL of test solution per challenge organism. Each tube of the solution to be tested is inoculated with a suspension of the test organism sufficient to provide a final count of $1\times10^5$ to $1\times10^6$ cfu/mL, the volume of the inoculum not exceeding 1 percent of the sample volume. Dispersion of the inoculum is ensured by vortexing the sample for at least 15 seconds. The inoculated product is stored at 10° C. to 25° C. Aliquots in the amount of 1.0 mL are taken of the inoculated product for determination of viable counts after certain time periods of disinfection.

The suspension is mixed well by vortexing vigorously for at least 5 sec. The 1.0 mL aliquots removed at the specified time intervals are subjected to a suitable series of decimal dilutions in validated neutralizing media. The suspensions are mixed vigorously and incubated for a suitable period of time to allow for neutralization of the microbial agent. The viable count of organisms is determined in appropriate dilutions by preparation of triplicate plates of trypticase soy agar (ISA) for bacteria and Sabouraud dextrose agar (SDA) for mold and yeast. The bacterial recovery plates are incubated at 30° C. to 35° C. for two to four days. The yeast recovery plates are incubated at 20° C. to 30° C. for two to four days. The mold recovery plates are incubated at 20° C. to 25° C. for three to seven days. The average number of colony forming units is determined on countable plates. Countable plates refer to 30 to 300 cfu/plates for bacteria and yeast, and 8 to 80 cfu/plate for mold except when colonies are observed only for the $10^0$ or $10^{-1}$ dilution plates. The microbial reduction is then calculated at the specified time points.

Preliminary Clinical Evaluation of Example No. 4

Twenty-three (23) subjects completed a two hour, dispensing study using PureVision® lenses from Bausch & Lomb, Inc., comparing the formulation of Example No. 4 to Opti-Free® Replenish MPS (control solution). Each well of the lens cases was pre-treated (a single, 4-hour minimum soak) with either test solution or control solution. For each case, the well treated with test solution was randomly determined and the other well received the control solution. All of the lenses were pre-treated (4-hour minimum soak), with either the test solution or control solution, in the pre-treated lens cases, following the same randomization used for the lens case wells.

Figure 2:
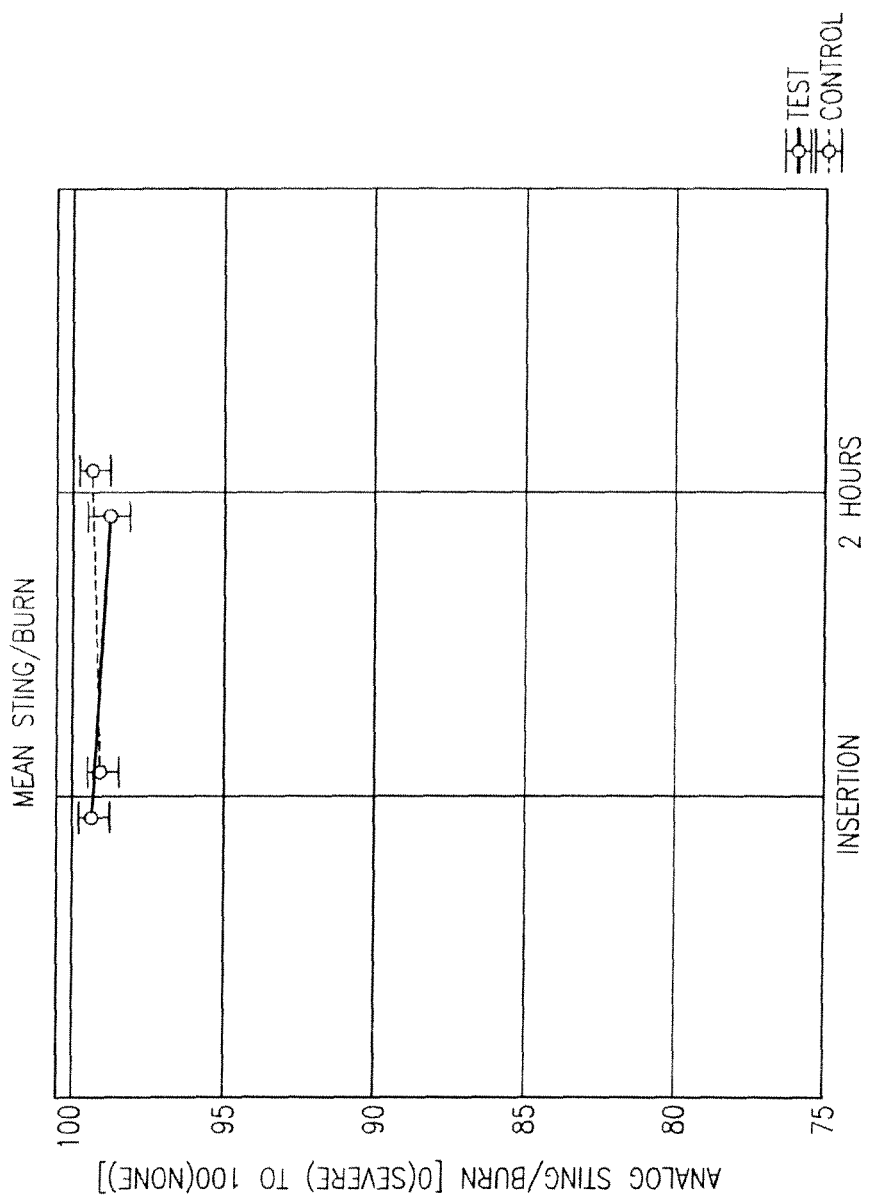
FIG. 2 is a plot showing a clinical comparison between a test solution and control solution for sting/burn at insertion of a contact lens and after two hours.
Figure 3:
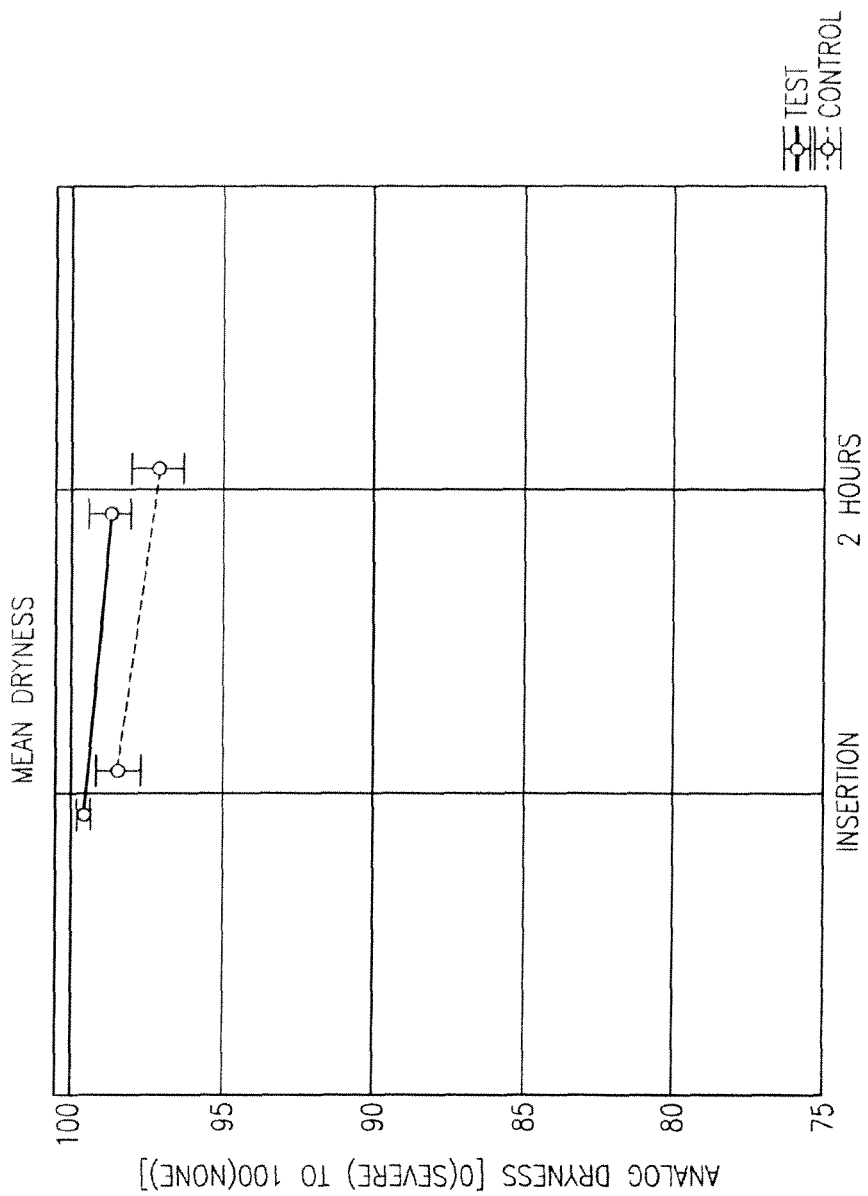
FIG. 3 is a plot showing a clinical comparison between a test solution and control solution for dryness at insertion of a contact lens and after two hours.
Figure 4A:
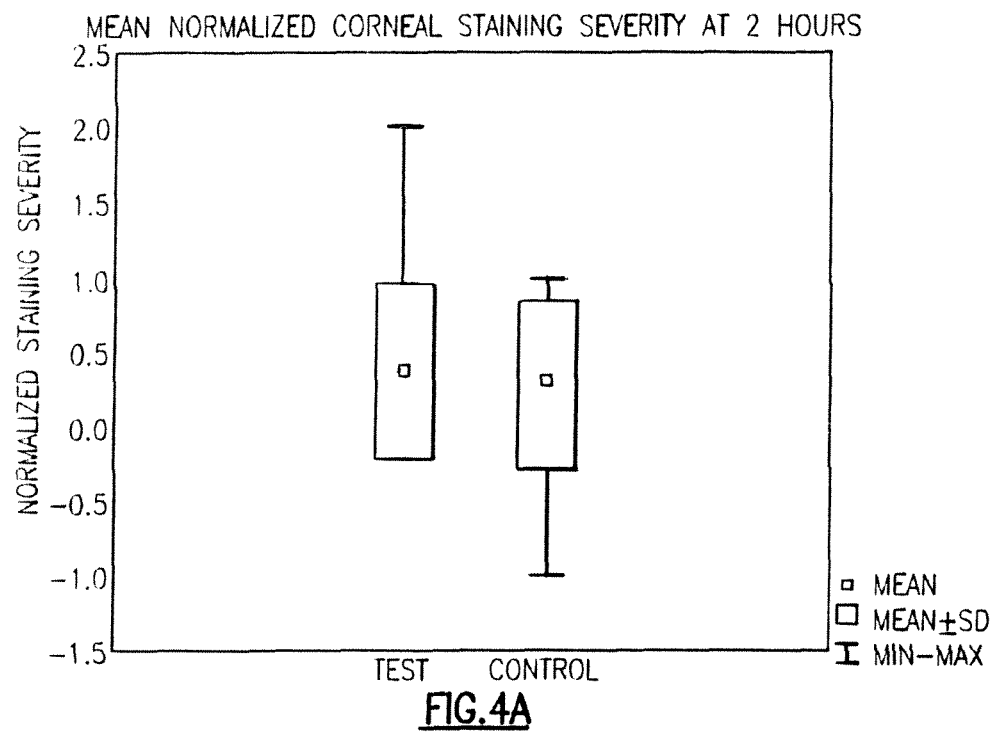
FIG. 4A is a plot showing a clinical comparison between a test solution and control solution in regard to normalized superficial punctate corneal staining severity at two hours.
Figure 4B:
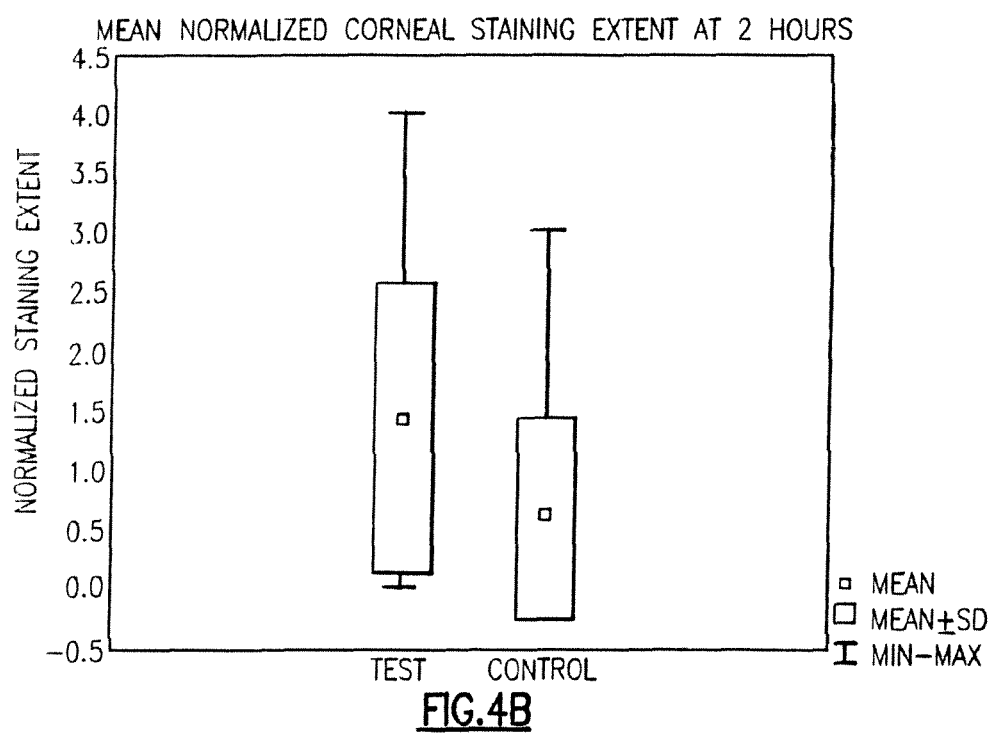
FIG. 4B is a plot showing a clinical comparison between a test solution and control solution in regard to normalized superficial punctate corneal staining extent at two hours.
Figure 5A:
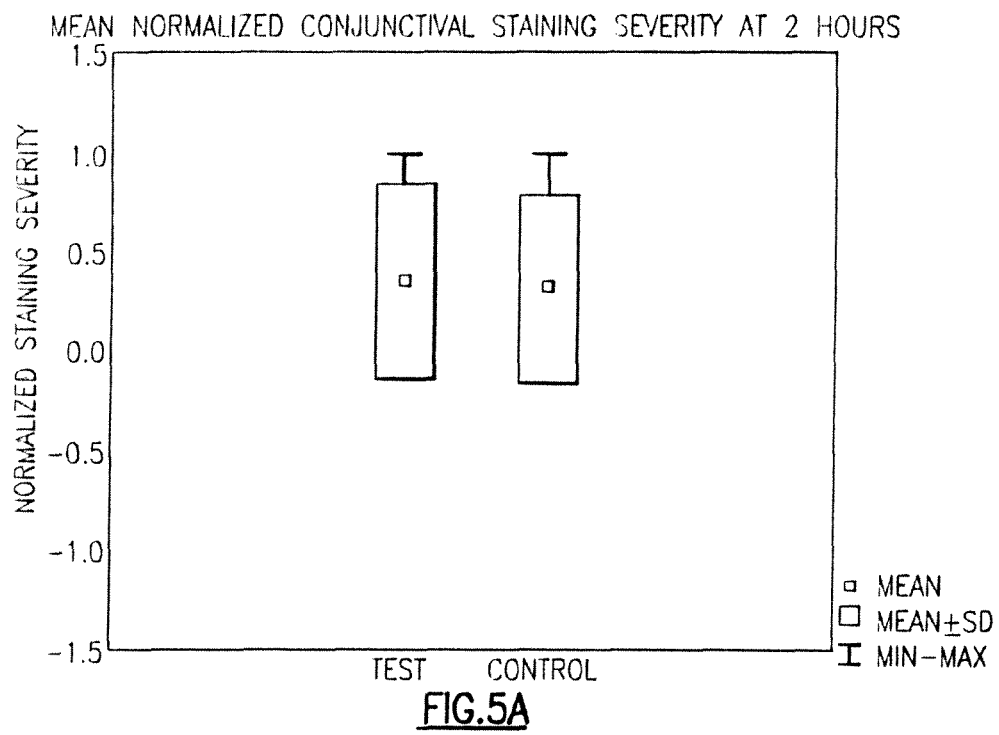
FIG. 5A is a plot showing a clinical comparison between a test solution and control solution in regard to normalized superficial punctate conjunctival staining severity at two hours.
Figure 5B:
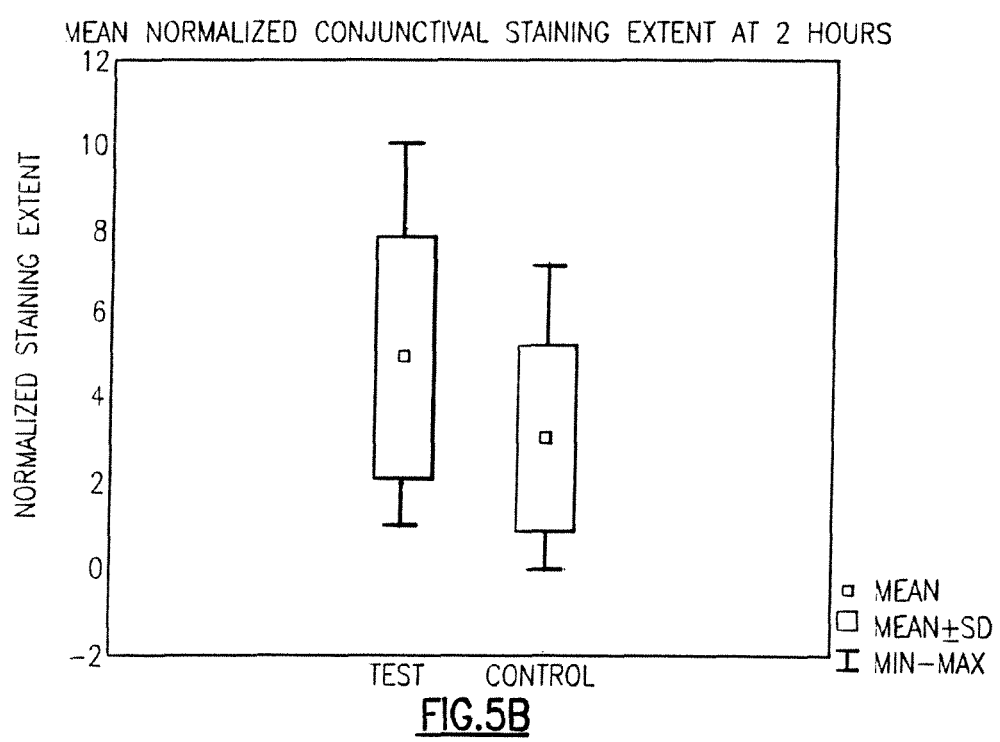
FIG. 5B is a plot showing a clinical comparison between a test solution and control solution in regard to normalized superficial punctate conjunctival staining extent at two hours.

Of the 23 subjects who completed the study, five (5) preferred the test solution and four (4) preferred the control at insertion of the lenses. Fourteen (14) stated no difference, FIG. 1. Also, there was no statistically significant difference for mean sting/burn between the test solution and the control solution eyes for the two hour duration of the test, FIG. 2. The test solution lenses exhibited statistically (but not clinically) significant less dryness than the control, FIG. 3. Prior to lens insertion, superficial punctate corneal staining was assessed with the slit lamp. After approximately 2 hours of lens wear, each subject returned. Lenses were removed, superficial punctate corneal staining profiles were reassessed with the slit lamp. There was no statistically significant difference for mean normalized corneal staining severity, or mean normalized conjunctival staining severity, between the test solution and the control solution eyes after two hours, FIGS. 4A and 5A, respectively. Test solution lenses did exhibit statistically (but not clinically) significant greater normalized corneal staining extent than the control, and statistically (but not clinically) significant greater normalized conjunctival staining extent, than the control solution eyes at two hours, FIGS. 4B and 5B, respectively.

Biocidal stand-alone stability data was obtained with Example No. 5.

TABLE 9

Four-hour biocidal stability in PET bottles at elevated temperatures.

| Time point | ° C. | Sa | Pa | Sm | Ca | Fs |
|---|---|---|---|---|---|---|
| $t_0$ | 25 | >4.8 | >4.7 | 3.3 | 2.4 | 4.2 |
| one month | 25 | >4.9 | >4.6 | >4.6 | 3.0 | 3.7 |
|  | 40 | >4.9 | >4.6 | >4.6 | 2.5 | 3.7 |
|  | 50 | 4.3 | >4.6 | 4.3 | 2.5 | 4.1 |
| two month | 25 | 4.0 | >4.6 | 3.3 | 2.7 | 3.2 |
|  | 50 | 4.0 | 3.5 | 3.5 | 2.0 | 3.0 |
| three month | 25 | >4.8 | >4.7 | 4.6 | 2.7 | 2.8 |
|  | 50 | 4.6 | >4.7 | 4.4 | 2.2 | 2.9 |
| four month | 25 | >4.9 | >4.7 | 3.8 | 3.0 | 3.5 |
|  | 40 | >4.9 | 4.7 | 3.5 | 2.3 | 4.0 |
|  | 50 | 4.0 | >4.7 | 3.7 | 1.7 | 3.1 |
| six month | 25 | >4.8 | >4.8 | 4.8 | 3.2 | 3.9 |
|  | 40 | >4.8 | >4.8 | 4.8 | 3.0 | 3.8 |
| nine month | 25 | 3.4 | >4.6 | 4.1 | 2.7 | 3.8 |
|  | 40 | 4.2 | >4.6 | 4.1 | 2.0 | 2.2 |
| $t_0$ | Opti-Free ® Replenish 25° C. | 3.6 | >4.6 | 3.0 | 1.6 | 3.1 |

Lens Compatibility Testing

TABLE 9

Lens compatibility data of commercial lenses with Example No. 5.

| Soft Contact Lens Type | Parameter | ISO Spec | 30 Cycles |
|---|---|---|---|
| ACUVUE ® 2 | Diameter | ±0.20 mm | In spec |
|  | Estimated Base Curve | ±0.20 mm | In spec |
| ACUVUE ® OASYS | Diameter | ±0.20 mm | In spec |
|  | Estimated Base Curve | ±0.20 mm | In spec |
| PureVision ® | Diameter | ±0.20 mm | In spec |
|  | Estimated Base Curve | ±0.20 mm | In spec |

Example Nos. 5 to 10

A biocidal efficacy study was conducted to investigate the activity of a modified formulation of Example 5 with the exception of the stated concentrations of PHMB and Hest G-18-O. The concentration of PHMB would vary from 0.5 ppm, 0.8 ppm and 1.3 ppm of PHMB, and the concentration of Hest G-18-O from 0.01 wt. % and 0.05 wt. %, Table 10. The biocidal profile of OptiFree® Replenish is also listed for comparison.

TABLE 10

Lens care solutions with glycereth-18-ethylhexanoate and PHMB.

| Example No. (PHMB/HestG18O) | S. aureus | P. aeruginosa | S. marcescens | C. albicans | F. solani |
|---|---|---|---|---|---|
| BBS w/0.5 PHMB | 2.1 | 3.0 | 2.3 | 0.9 | 0.9 |
| BBS w/0.8 PHMB | 2.4 | 3.4 | 2.4 | 1.5 | 1.7 |
| BBS w/1.3 PHMB | 3.1 | 3.8 | 2.7 | 2.1 | 2.2 |
| 5 (0.5/0.01) | 2.4 | >4.8 | 3.2 | 1.7 | 1.1 |
| 6 (0.8/0.01) | 3.1 | 3.7 | 3.1 | 2.0 | 1.9 |

TABLE 10-continued

Lens care solutions with glycereth-18-ethylhexanoate and PHMB.

| Example No. (PHMB/HestG18O) | S. aureus | P. aeruginosa | S. marcescens | C. albicans | F. solani |
|---|---|---|---|---|---|
| 7 (1.3/0.01) | 4.2 | 3.7 | 3.5 | 2.6 | 3.1 |
| 8 (0.5/0.05) | 2.8 | 4.3 | 3.4 | 1.6 | 0.9 |
| 9 (0.8/0.05) | 3.9 | 3.4 | 3.8 | 2.4 | 2.3 |
| 10 (1.3/0.05) | >4.9 | 4.8 | 4.5 | 2.9 | 4.0 |
| OF Replenish | 3.8 | >4.8 | 3.4 | 0.8 | 2.0 |

We claim:

1. An ophthalmic composition with antimicrobial activity to *Staphylococcus aureus*, *Pseudomonas aeruginosa*, *Serratia marcescens*, *Candida albicans*, and *Fusarium solani*, comprising borate buffered saline, about 2 ppm alexidine and 0.05 wt. % to 0.1 wt. % of glycereth-18-ethylhexanoate.

2. The composition of claim 1 further comprising hyaluronic acid present from 0.005 wt. % to 0.1 wt. %.

3. The composition of claim 1 further comprising α-[4-tris(2-hydroxyethyl)-ammonium chloride-2-butenyl]poly[1-dimethyl ammonium chloride-2-butenyl]-ω-tris(2-hydroxyethyl) ammonium chloride, which is present from 0.5 ppm to 3 ppm.

4. The composition of claim 1 further comprising 0.01 wt. % to 1.0 wt. % of an amphoteric surfactant of general formula II

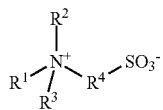

II wherein $R^1$ is R or —$(CH_2)_n$—NHC(O)R, wherein R is a $C_8$-$C_{16}$ alkyl optionally substituted with hydroxyl and n is 2, 3 or 4; $R^2$ and $R^3$ are each independently selected from methyl, ethyl, propyl or iso-propyl; and $R^4$ is a $C_2$-$C_8$ alkylene optionally substituted with hydroxyl.

5. The composition of claim 4 wherein $R^1$ is R; $R^2$ and $R^3$ are each methyl; and $R^4$ is a $C_2$-$C_4$ alkylene.

6. The composition of claim 1 further comprising dexpanthenol, sorbitol, glycolic acid, 2-amino-2-methyl-1,3-propanediol or any mixture thereof.

7. The composition of claim 1 further comprising propylene glycol, hydroxypropyl guar or myristamidopropyl dimethylamine.

8. The composition of claim 1 further comprising hydroxypropylmethyl cellulose.

9. An aqueous contact lens care solution composition with antimicrobial activity to *Staphylococcus aureus*, *Pseudomonas aeruginosa*, *Serratia marcescens*, *Candida albicans*, and *Fusarium solani*, comprising:
   borate buffered saline;
   about 2 ppm of alexidine;
   0.5 ppm to 3 ppm α-[4-tris(2-hydroxyethyl)-ammonium chloride-2-butenyl]poly[1-dimethyl ammonium chloride-2-butenyl]-ω-tris(2-hydroxyethyl) ammonium chloride; and
   0.05 wt. % to 0.1 wt. % of glycereth-18-ethylhexanoate.

10. The contact lens care solution of claim 9 further comprising a nonionic surfactant selected from poloxamer, poloxamine or any combination thereof.

11. A method of cleaning and disinfecting a contact lens, the method comprising soaking the contact lens in the ophthalmic composition of claim 1 for at least two hours.

12. The method of claim 11 further comprising inserting the cleaned and disinfected contact lens into the eye without rinsing the lens after soaking.

13. The method of claim 11 wherein the ophthalmic composition further comprises 0.5 ppm to 3 ppm α-[4-tris(2-hydroxyethyl)-ammonium chloride-2-butenyl]poly[1-dimethyl ammonium chloride-2-butenyl]-ω-tris(2-hydroxyethyl) ammonium chloride.

* * * * *